(12) United States Patent
Rodrigues

(10) Patent No.: US 11,327,464 B2
(45) Date of Patent: May 10, 2022

(54) SYSTEMS AND METHODS OF THREE-DIMENSIONAL PRINTING OF COLLIMATORS USING ADDITIVE APPROACHES

(71) Applicant: Siemens Medical Solutions USA, Inc., Malvern, PA (US)

(72) Inventor: Miesher Rodrigues, Buffalo Grove, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 132 days.

(21) Appl. No.: 15/733,430

(22) PCT Filed: Mar. 8, 2018

(86) PCT No.: PCT/US2018/021451
§ 371 (c)(1),
(2) Date: Jul. 28, 2020

(87) PCT Pub. No.: WO2019/172907
PCT Pub. Date: Sep. 12, 2019

(65) Prior Publication Data
US 2021/0096536 A1    Apr. 1, 2021

(51) Int. Cl.
*G05B 19/4099* (2006.01)
*B33Y 50/02* (2015.01)
(Continued)

(52) U.S. Cl.
CPC ........ *G05B 19/4099* (2013.01); *B29C 64/393* (2017.08); *B33Y 50/02* (2014.12);
(Continued)

(58) Field of Classification Search
None
See application file for complete search history.

(56) References Cited

U.S. PATENT DOCUMENTS

| | | |
|---|---|---|
| 2003/0072416 A1 | 4/2003 | Eidam et al. |
| 2004/0156479 A1 | 8/2004 | Hoheisel et al. |

(Continued)

OTHER PUBLICATIONS

International Search Report for corresponding application No. PCT/US2018/021451, dated May 25, 2018.
(Continued)

*Primary Examiner* — Thomas C Lee
*Assistant Examiner* — Syed A Warsi

(57) ABSTRACT

A method of manufacturing a collimator (134) on a three-dimensional printer (510) includes obtaining design specifications (536) for the collimator, the design specifications including a channel perimeter pattern and an overall collimator thickness, determining a first quantity of deposit layer permutation types based on the channel perimeter pattern, determining a respective second quantity of permutation layer elements (310, 320, 330) for each respective one of the deposit layer permutations, generating respective sets of sequences for each respective one of the deposit layer permutations, the number of sets equal to the respective second quantity for the corresponding deposit layer permutations, assembling the respective sets of sequences into a three-dimensional print file (538), providing the three-dimensional file to the three-dimensional printer, and manufacturing the collimator by depositing additive layers of material based on contents of the three-dimensional file. A system for implementing the method and a non-transitory computer-readable medium are also disclosed.

15 Claims, 6 Drawing Sheets

(51) Int. Cl.
    *B33Y 80/00*         (2015.01)
    *B29C 64/393*      (2017.01)
    *G02B 27/30*       (2006.01)
    *B33Y 10/00*       (2015.01)
    *B29L 11/00*       (2006.01)

(52) U.S. Cl.
    CPC .............. *B33Y 80/00* (2014.12); *G02B 27/30* (2013.01); *B29L 2011/00* (2013.01); *B33Y 10/00* (2014.12); *G05B 2219/35134* (2013.01); *G05B 2219/49023* (2013.01)

(56) References Cited

U.S. PATENT DOCUMENTS

| | | | |
|---|---|---|---|
| 2008/0233966 A1* | 9/2008 | Scheim | H04L 5/0058 455/452.1 |
| 2014/0341333 A1 | 11/2014 | Wang et al. | |
| 2015/0115494 A1* | 4/2015 | Deych | G21K 1/025 264/109 |
| 2016/0178983 A1* | 6/2016 | Alloatti | G02F 1/377 385/122 |
| 2016/0370791 A1 | 12/2016 | Revanur et al. | |

OTHER PUBLICATIONS

Asadi-Eydivand, M. et al. "Optimal Design of a 3D-Printed Scaffold Using Intelligent Evolutionary Algorithms" Applied Soft computing, vol. 39.
Extended European Search Report for Corresponding EP Application No. EP18909218, dated Feb. 11, 2021.

\* cited by examiner

SYSTEMS AND METHODS OF THREE-DIMENSIONAL PRINTING OF COLLIMATORS USING ADDITIVE APPROACHES

BACKGROUND

Single Photon Emission Computed Tomography (SPECT) imaging systems include a collimator in the path of radioisotope emitted by an object-under-study and a detector (e.g., a photomultiplier tube, or the like). The choice of collimator design can have an impact on the sensitivity and resolution of the SPECT system.

The collimator acts as the front-end of a gamma camera, and has a big impact on the signal-to-noise ration of the captured image. The collimator functions to spatially control the propagation direction (i.e., field-of-view) of the gamma rays reaching the detector—similar to a lens used in visible photon wavelengths. SPECT collimators are typically formed from radiation-absorbent material, where non-absorbed photons can reach the detector.

FIG. 1 is a diagram of conventional SPECT scanner imaging system 100. SPECT scanner system 100 includes gantry 120 to which two or more gamma cameras 130a, 130b are attached, although other numbers of gamma cameras can be used. Detector 132 in the gamma ray camera detects gamma photons 140 emitted by a radioisotope within the body of a patient 145 lying on a bed 150. Collimator 134 is positioned between the emitted photon and the detector. Bed 150 is slidable along axis-of-motion A. At respective bed positions (i.e., imaging positions), a portion of the body of patient 145 is positioned between gamma cameras 130a, 130b and an image of that body portion is captured.

Control processor 110 can execute instructions to control operation of the SPECT scanning system. Motion control/automation module 112 can control motors, servos, and encoders to cause gamma cameras 130a, 130b to rotate along gantry 120, and to move bed 150 along an axis-of-motion (arrow A). Data acquisition/image processing module 114 can acquire projection data at defined imaging position points during the rotation of gamma cameras 130a, 130b and/or the shifting of bed 150. The acquired data can be stored in memory 118. Imaging processing algorithms can manipulate the stored projection data to reconstruct a 3D image. The reconstructed 3D image can be displayed on an interactive display controlled by operator interface/display module 116.

Conventional attempts to use commercially-available, off-the-shelf three-dimensional ("3D") printers to produce the collimator patterns commonly used in SPECT have not achieved satisfactory results. Conventional 3D printing of collimators fails to meet the quality required for medical imaging (e.g., tolerances, uniformity, manufacturability, etc.).

There are significant challenges in making use of commercially-available, additive processes to produce medical-modality collimators on a 3D printer. One reason is that the required tolerances cannot be guaranteed using 3D printers' additive processes due to the high viscosity of the extruded filament print material, which is made even higher when imbedded with high-density and high-atomic number ("Z") materials (required to increase the attenuation of ionizing radiation). Limitations controlling the position and speed of the extruding printhead relative to the flow of the extruded material also contribute to the challenges. Because of these factors, the conventional approach of producing stereolithography files (e.g., STL format) directly from 3D CAD files is not a viable solution. Further, conventional approaches to manufacturing collimators by 3D printing fail to yield devices that meet quality requirements of medical imaging (tolerances, uniformity, manufacturability, etc.) using off-the-shelf components.

In recent years, vendors of 3D printed collimators have been proposing green manufacturing processes (e.g., Pb-free and RoHS-compliant) that require special printing processes which require significant investment and add cost to the end products. None of these processes have been successfully produced in scale to replace current available lead collimators. The cost for these conventional 3D printed collimators is greater than existing lead collimators.

There is a need in the art to quickly, and accurately create medical-modality collimators by applying layered 3D printing techniques using information contained in a stereolithography file.

DETAILED DESCRIPTION

Embodying systems and methods implement one or more layered-permutation sequence algorithms that specify the content of a stereolithography ("STL") file used to instruct a 3D printer to produce a collimator using an additive, layered process. The printed collimator is extruded layer by layer using 3D printer filament, to form a collimator of suitable thickness for its intended medical modality. Systems and methods specify each layer representation within the STL file in a predetermined order to achieve a collimator capable of operating within required performance specifications.

A collimator manufactured by these techniques can be applicable for various medical modalities (e.g., SPECT, CT, and others). For purposes of this disclosure, a SPECT system collimator will be discussed. However, the invention is not so limited, it should be readily understood that other medical-modality collimators are within the scope of this disclosure.

In accordance with embodiments, a 3D printed collimator with required tolerances and overall quality, and having a large field-of-view can be produced using off-the-shelf components from an STL file created by embodying algorithms. Embodying system and methods can have direct applications in fast-prototyping operable collimators for test/prove-out of new designs. Embodying approaches distinguish over conventional techniques by being able to quickly print and test new collimator designs (for performance compatibility/impact with improved image reconstruction algorithms).

This distinction over the prior art can be of great value to improving current and future SPECT systems and applications. Embodying systems and methods make possible the manufacture of medium-energy SPECT collimators using commercially available 3D printing off-the-shelf components.

Figure 1:
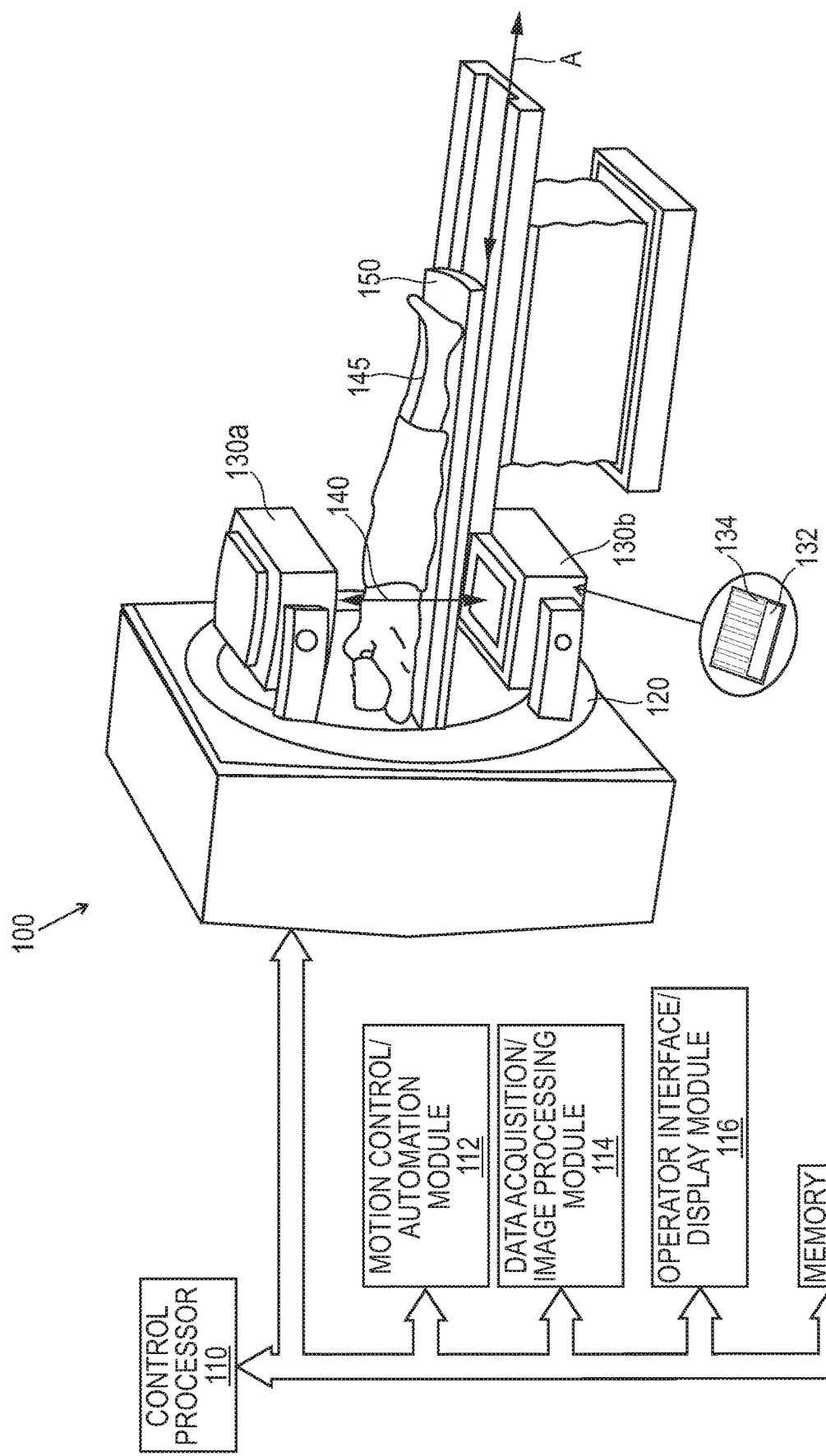
FIG. 1 depicts a conventional SPECT scanner imaging system.
Figure 2A:
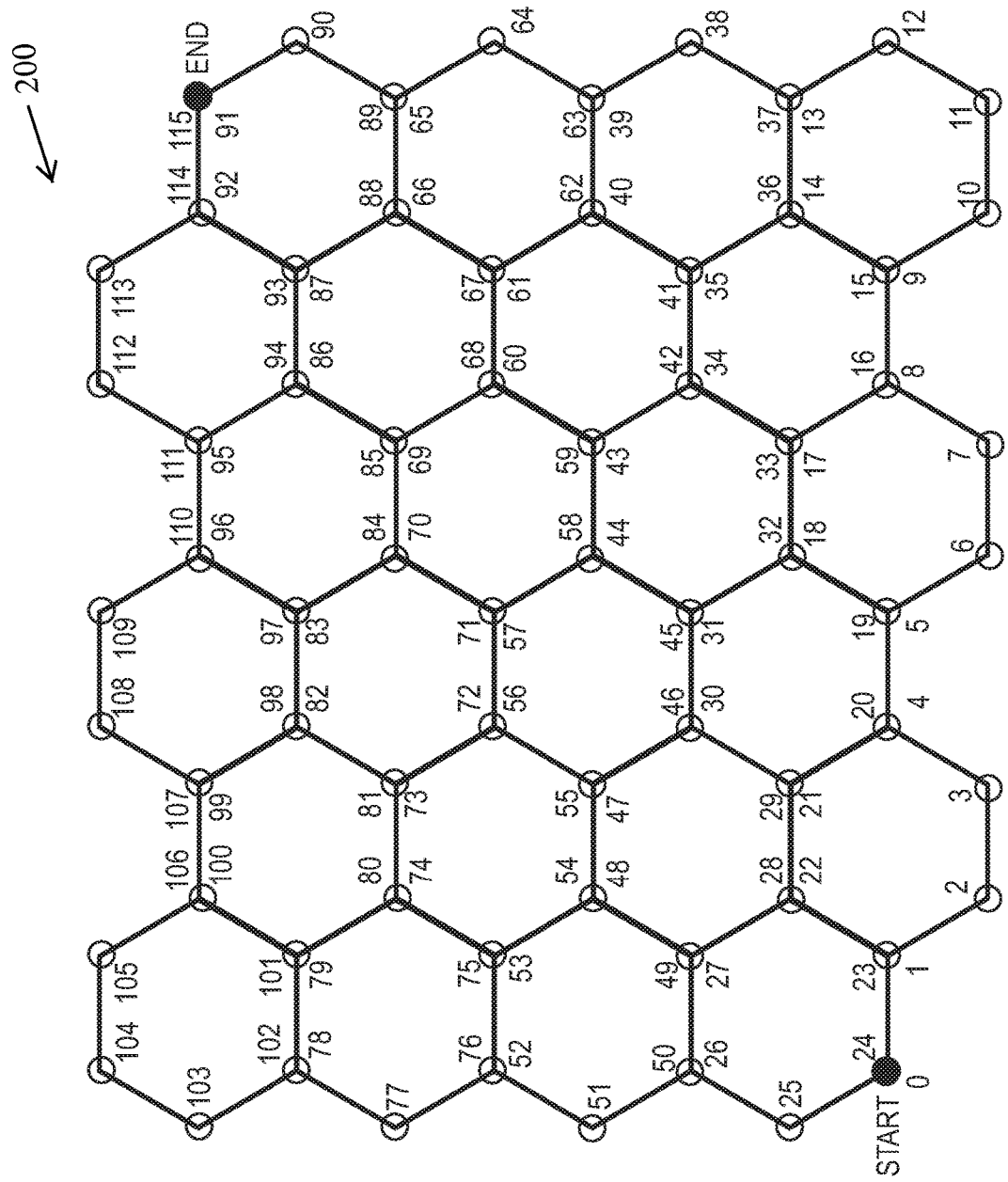
FIG. 2A depicts a conventional 3D printer trajectory path.

FIG. 2A depicts conventional 3D printer trajectory path 200, which illustrates the segments covered by the printhead. The printhead begins a forward trajectory at position 0 and ends its travel at position 115; retraces itself in a reverse trajectory from position 115 to position 0; and repeats forward and reverse trajectories until the layered material is at a specified height.

Figure 2C:
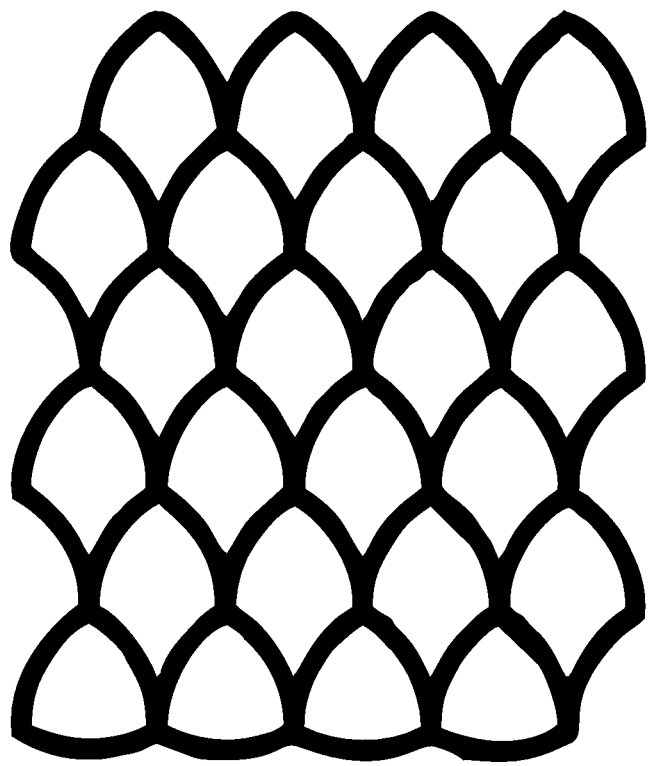
FIG. 2C depicts a synthesized cumulative result for the trajectory path of FIG. 2A.
Figure 2B:
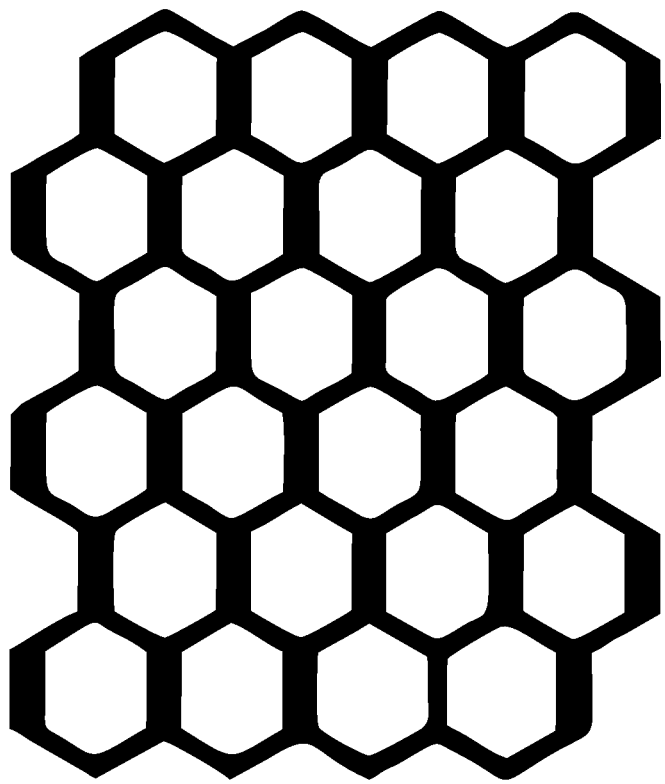
FIG. 2B depicts a predicted resulting cumulative deposit for the trajectory path of FIG. 2A.

FIG. 2B depicts predicted 3D printed pattern. This predicted pattern can be an idealized version from the contents of the CAD drawing used to create the conventional STL file. FIG. 2C depicts an illustration of actual 3D printed pattern, which is the result of the conventional approach to 3D printing of the collimator.

As illustrated by the examples of FIGS. 2A-2C, under conventional techniques, the required size and tolerances of collimators are difficult (perhaps impossible) to maintain using the conventional direct-conversion of CAD files into STL files while using traditional 3D printing methods (forward trajectory, reverse trajectory, and repeat cycle) with off-the-shelf components.

Drawbacks in the conventional approaches result from, for example, the 3D printhead is required to re-trace itself along the same path during the additive process detailed in the conventional STL file; and/or maneuvering through sharp turns (e.g., about 60° or greater) during its trajectory. These features are not properly achieved when created by a 3D printer extruding conventional materials per information provided by a conventional STL file.

Figure 3A:
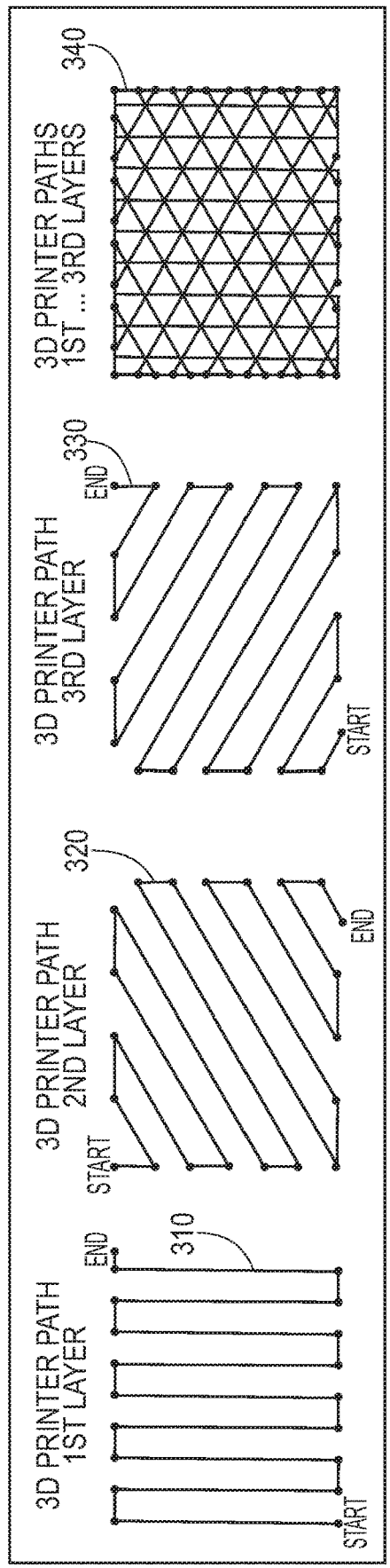
FIG. 3A depicts multiple layers of a 3D printer trajectory path, and its predicted cumulative deposit in accordance with embodiments.

FIG. 3A depicts multiple layers 310, 320, 330 of a 3D printer trajectory path, and predicted cumulative deposit 340 in accordance with embodiments. Each of multiple layers 310, 320, 330 represents a respective trajectory path for the printhead, where each layer describes a respective path along which the printhead does not retrace itself to produce that respective individual layer. For this example, when overlapped the multiple layers form a triangular lattice.

Layer 310 depicts a printhead path with two connected sets of about parallel lines, where one set of lines is orthogonal to the other. The printhead moves along the trajectory path. Layer 320 depicts a printhead path with one set of lines rotated clockwise diagonally (about 60°) from its position in layer 310. Similarly, layer 320 depicts a printhead path with the same set of lines rotated counterclockwise diagonally (about –60°) from its position in layer 310.

The triangular-hole predicted cumulative deposit 340 is formed by stacking successive groupings of these three different layers 310, 320, 330 one grouping after the other grouping. These layers are positioned relative to each other with respect to the horizontal plane of deposit so that the overlapping portions of the 3D-printed layers intercept at about their center. In accordance with embodiments, the groupings can follow a non-repeating permutation sequence; or a random sequence.

The trajectory path for each of the multiple layers is determined by an embodying algorithm (described below). The algorithm receives design specification parameters for a medical-modality collimator. The design specifications can be in the form of a CAD file describing the design of the collimator to be printed on the 3D printer. In other implementations, the design specifications can be stored as one or more database records (e.g., objects, tabular data, etc.), or other formats.

Figure 3B:
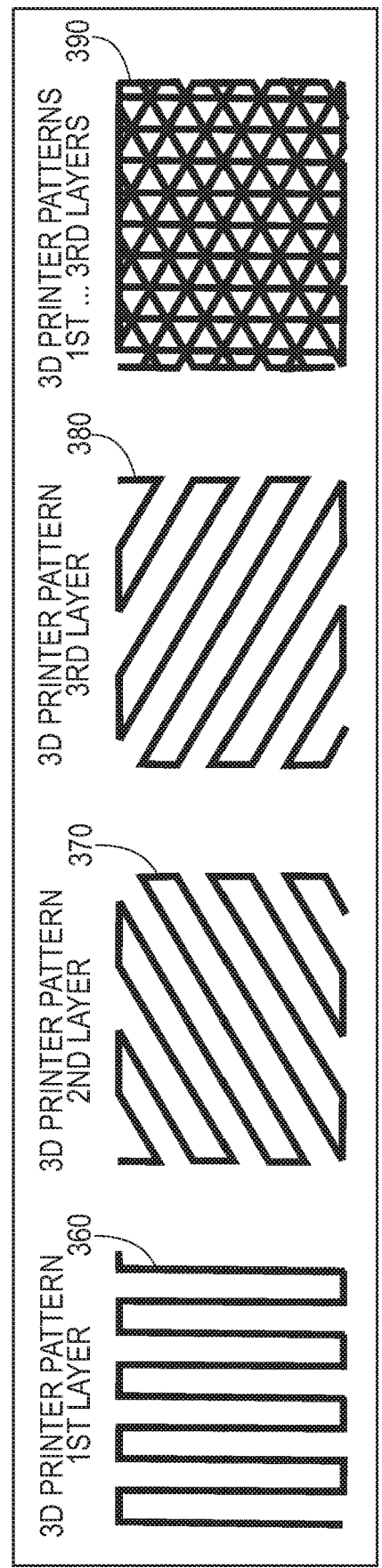
FIG. 3B depicts synthesized results for individual layers and a synthesized cumulative result for the multiple layers depicted in FIG. 3A in accordance with embodiments.

FIG. 3B depicts synthesized results 360, 370, 380 for individual layers 310, 320, 330 and a synthesized cumulative result 390 for the multiple layers depicted in FIG. 3A in accordance with embodiments.

The conventional, synthesized cumulative result illustrated in FIG. 2C (produced by multiple cycles retracing along the same printhead path) does not result in a collimator having straight septa of equal length to form the hexagonal channels depicted in FIG. 2B. However, synthesized cumulative result 380 produced in accordance with embodiments results in straight septa of about equal length to form the perimeter of a triangle with about equal sides, resulting in collimator having about triangular matrix of channels.

In accordance with embodiments, a physical collimator represented by synthesized cumulative result 390 can be produced by stacking groupings of printer path layer 310, printer path layer 320, and printer path layer 330 to create triangular patterns. The deposition of the extruded material within the collimator's field-of-view is along straight lines, with all turns made outside the field-of-view. Multiple renditions of the stacked grouped layers are deposited to build the septa walls to the desired height. In accordance with implementations, collimators with hexagonal, square, triangular, or other perimeter channels can be produced.

In accordance with embodiments, the ordering of the multiple paths within each stacked grouping can be varied between groups. In some implementations, the ordering within a stack grouping can be sequential (e.g., ABC, ABC, ABC, . . . ), stepped (e.g., ABC, BCA, CAB, . . . ), random (ABC, BAC, CBA, . . . ), or a non-repeating permutation— where "A", "B" and "C" represent different types of 3D printhead trajectory path patterns (e.g., layers 310, 320, 330). The variation in stack grouping can reduce manufacturing imaging artifacts in the 3D printed collimator, thus improving its overall performance. The thickness of layers, and/or successive layers can also reduce manufacturing imaging artifacts and, thus, improve the collimator performance.

For a given design specification of a medical-modality collimator, the following parameters can be determined:
  p!: the number of permutations of p types of layers without repetition;
  n: the number of 3D printed layers;
  p: the number of types of layers;
  d: the thickness of a 3D-printed layer; and
  t: the overall collimator thickness.

For example, for a triangular-hole collimator, p=3 (layers) and p!=6 (quantity of layer permutation types). In accordance with one implementation, the sequence of permutations can be:
  Layer grouping permutation #1: [A,B,C];
  Layer grouping permutation #2: [B,A,C];
  Layer grouping permutation #3: [C,A,B];
  Layer grouping permutation #4: [A,C,B];
  Layer grouping permutation #5: [B,C,A];
  Layer grouping permutation #6: [C,A,B].

Based on the collimator design specifications, embodying systems and methods can determine the number of layer permutations, and the grouping pattern for within each layer. For example, a non-repeating permutation sequence can be determined as follows:

The quantity of non-repeating permutation sequences (l) can be pre-generated for storage in memory:

$$k_0 = p!^0 \times (p \times p!)$$

$$k_1 = p!^1 \times (p \times p!)$$

$$k_2 = p!^2 \times (p \times p!)$$

* * *

$$k_l = p!^l \times (p \times p!)$$

Where $k_l$ represents the quantity of elements of the $l^{th}$ permutation sequence. For instance, for p=3, $k_0$=18:
[A,B,C,B,A,C,C,A,B,A,C,B,B,C,A,C,A,B]

$k_1$=108:
[A,B,C,B,A,C,C,A,B,A,C,B,B,C,A,C,A,B,C,A,B,A,C,B, A,B,C,B,A,C,B, C,A,C,A,B,B,C,A,C,A,B,A,B,C,B,A, C,C,A,B,A,C,B,A,B,C,B,A,C,B,C, A,C,A,B,C,A,B,A, C,B,C,A,B,A,C,B,B,C,A,C,A,B,A,B,C,B,A,C,B,C,A, C,A,B,A,B,C,B,A,C,C,A,B,A,C,B]

and, $k_2$=648:
[A,B,C,B,A,C,C,A,B,A,C,B,B,C,A,C,A,B,C,A,B,A,C,B, A,B,C,B,A,C,B, C,A,C,A,B,B,C,A,C,A,B,A,B,C,B,A, C,C,A,B,A,C,B,A,B,C,B,A,C,B,C, A,C,A,B,C,A,B,A, C,B,C,A,B,A,C,B,B,C,A,C,A,B,A,B,C,B,A,C,B,C,A, C,A,B,A,B,C,B,A,C,C,A,B,A,C,B,B,C,A,C,A,B,A,B, C,B,A,C,C,A,B,A, C,B,A,B,C,B,A,C,B,C,A,C,A,B,C, A,B,A,C,B,A,B,C,B,A,C,C,A,B,A,C, B,B,C,A,C,A,B, C,A,B,A,C,B,A,B,C,B,A,C,B,C,A,C,A,B,C,A,B,A,C, B, B,C,A,C,A,B,A,B,C,B,A,C,B,C,A,C,A,B,A,B,C,B, A,C,C,A,B,A,C,B,C, A,B,A,C,B,B,C,A,C,A,B,A,B,C, B,A,C,B,C,A,C,A,B,A,B,C,B,A,C,C,A, B,A,C,B,A,B, C,B,A,C,C,A,B,A,C,B,B,C,A,C,A,B,C,A,B,A,C,B,A, B,C, B,A,C,B,C,A,C,A,B,B,C,A,C,A,B,A,B,C,B,A,C, C,A,B,A,C,B,A,B,C,B, A,C,B,C,A,C,A,B,C,A,B,A,C, B,A,B,C,B,A,C,C,A,B,A,C,B,B,C,A,C,A, B,C,A,B,A, C,B,A,B,C,B,A,C,B,C,A,C,A,B,C,A,B,A,C,B,B,C,A, C,A,B, A,B,C,B,A,C,B,C,A,C,A,B,A,B,C,B,A,C,C,A, B,A,C,B,B,C,A,C,A,B,A, B,C,B,A,C,C,A,B,A,C,B,A, B,C,B,A,C,B,C,A,C,A,B,C,A,B,A,C,B,B,C, A,C,A,B, A,B,C,B,A,C,C,A,B,A,C,B,A,B,C,B,A,C,B,C,A,C,A, B,C,B,A,C,C,A,B,A,C,B,A,C,B,C,A,C,A,B,A, B,C,B,A,C,C,A,B,A,C,B,B,C,A,C,A,B,C,A,B,A,C,B, A,C,B,C,A,C,A,B,A,C,B,B, C,A,C,A,B,C,A,B,A,C, B,A,B,C,B,A,C,B,C,A,C,A,B,B,C,A,C,A,B,A,B, C,B, A,C,C,A,B,A,C,B,A,B,C,B,A,C,B,C,A,C,A,B,C,A,B, A,C,B]

These sequences are generated using permutations of previously permutated sequences. The following is an embodying step-by-step description:

1) Beginning with different types of layers A, B, C (e.g., layer 310, layer 320, layer 330), define an initial set of sequences A', B' and C' (e.g., A'=A, B'=B, and C'=C): A'=[A], B'=[B], C'=[C];

2) Generate a non-repeating sequence of "ABC's" based on previous values of "A'B'C's", obtained from Step 1, where the base permutation sequence (A'B'C') does not change: [A',B',C']; [B',A',C']; [C',A',B']; [A',C',B']; [B',C',A']; [C',A',B'];

3) Define new values for A', B' and C', based on the previous step, by subdividing the previous sequence into three consecutive regions: A'=[A,B,C,B,A,C], B'=[C,A,B,A, C,B], C'=[B,C,A,C,A,B] (see $k_0$=18 above);

4) Generate a non-repeating sequence of "ABC's" based on values of "A'B'C's" obtained from previous step, where the base permutation sequence "A'B'C's" does not change: [A',B',C']; [B',A',C']; [C',A',B']; [A',C',B']; [B',C',A']; [C',A', B'] (see $k_1$=108 above);

5) Define A', B' and C' with new values, based on previous step, by subdividing the previous sequence in three consecutive regions:
A'=[A,B,C,B,A,C, C,A,B,A,C,B, B,C,A,C,A,B,C,A,B,A, C,B, A,B,C,B,A,C, B,C,A,C,A,B]
B'=[B,C,A,C,A,B, A,B,C,B,A,C, C,A,B,A,C,B,A,B,C,B, A,C, B,C,A,C,A,B, C,A,B,A,C,B]
C'=[C,A,B,A,C,B, B,C,A,C,A,B, A,B,C,B,A,C,B,C,A,C, A,B, A,B,C,B,A,C, C,A,B,A,C,B]

6) Generate a non-repeating sequence of ABC based on values of A'B'C' obtained from the previous step, where the base permutation sequence A'B'C' does not change: [A',B', C']; [B',A',C']; [C',A',B']; [A',C',B']; [B',C',A']; [C',A',B'] (see $k_2$=648 above)

7) Repeat above steps until a sequence is generated to satisfy the design specifications for the collimator based on layer thickness d, and the overall collimator thickness t, (i.e., k>t/d).

Knowing the pre-generated permutation sequences (steps 1-7), a 3D print sequence for the STL file can be assembled based on a ratio of the overall collimator thickness to the layer thickness (t/d), and the number of members of each permutation (kg):

If m=(t/d)≤$k_0$, grab a quantity of m sequence elements from $k_0$. For instance, if m=12, the sequence of layers can be the first twelve elements of sequence $k_0$—[A, B,C,B,A,C,C,A,B,A,C,B].

If $k_1$≥m=(t/d)>$k_0$, grab a quantity of m sequence elements from $k_1$. For instance, if m=30, the sequence of layers consists of the first 30 elements of sequence $k_1$—[A, B,C,B,A,C,C,A,B,A,C,B,B,C,A,C,A,B,C,A,B,A,C,B, A,B,C,B,A,C].

If $k_2$≥m=(t/d)>$k_1$, grab a quantity of m sequence elements from $k_2$. For instance, if m=640, the sequence of layers consists of the first 640 elements of sequence $k_2$.

Figure 4:
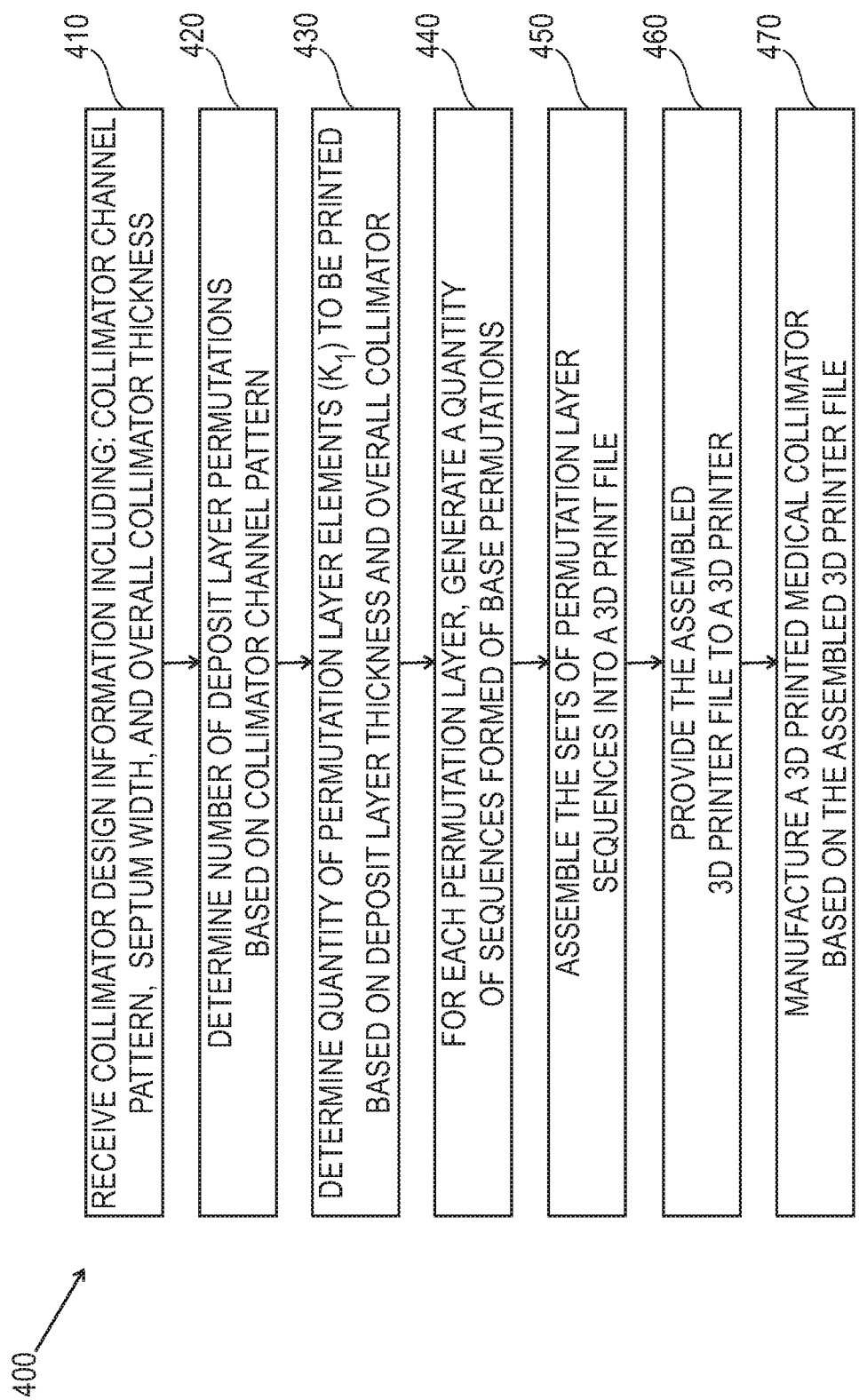
FIG. 4 depicts a process to create a 3D print file in accordance with some embodiments.

FIG. 4 is a flowchart for process 400 to create a STL file for manufacturing a printed collimator in accordance with embodiments. The STL file includes instructions to control a 3D printer to produce groupings of layered printhead paths in accordance with embodiments.

The design specification parameters for a medical-modality collimator are received, step 410. The parameters can be obtained from a CAD file, database record(s), or other memory and/or file. Parameters can include the collimator channel pattern (e.g., square, triangular, hexagonal, etc.), the septum wall width, overall collimator thickness.

Determine the number of deposit layer permutation sequence, step 420. The number of layers is related to the number of walls to form the channel (e.g., triangular channel has 3 permutation sequences. Calculate the number of permutation layer elements (1Q) to be deposited for each layer, step 430. The number of permutation layers is related to the deposit layer thickness and the overall collimator design specification thickness. For each permutation layer, step 440, generate a quantity of sequences formed from a base permutation sequence. The quantity of sequences is dependent on the layer thickness.

Once the sequences for each permutation layer is generated, these permutation layers can be assembled, step 450, to form a 3D printer file, e.g., a STL format file and/or object. The assembled 3D print file can be provided, step 460, to a 3D printer. By following the permutation sequences and layers specified in the 3D print file, a 3D printer can manufacture, step 470, a medical collimator based on the assembled sets of permutation layers.

Figure 5:
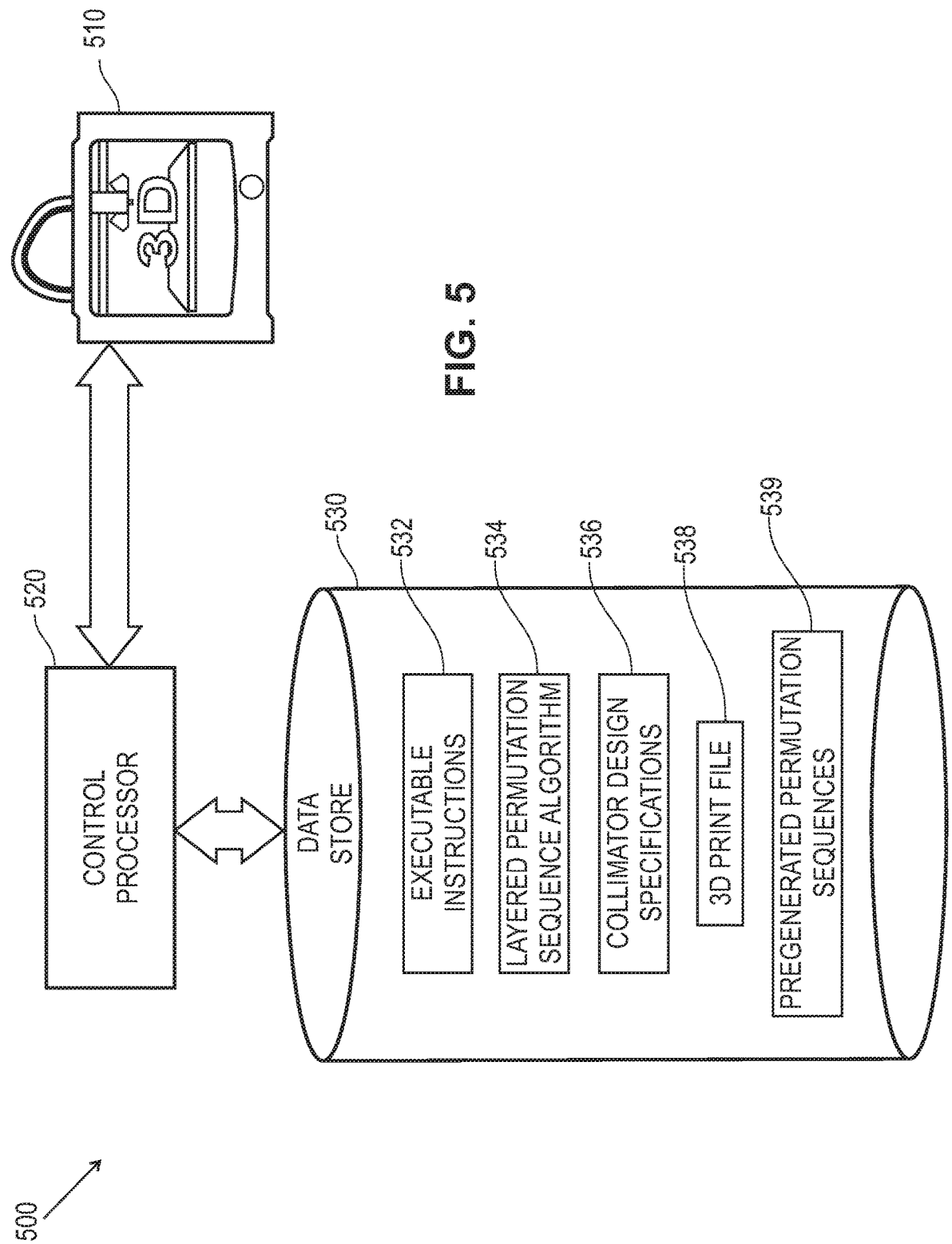
FIG. 5 depicts a 3D printer system for producing a collimator in accordance with embodiments.

FIG. 5 depicts 3D printer system 500 for producing a medical-modality collimator in accordance with embodiments. System 500 includes 3D printer 510 in communication across an electronic network (not shown) with control processor 520. Control processor 520 can access executable instructions 532 in data store 530, which causes the control processor to control components of system 500. Dedicated hardware, software modules, and/or firmware can implement embodying services disclosed herein.

Layered-sequence algorithm 534 can be executed by the control processor to perform the steps outlined above to create 3D print file 538, which specifies to 3D printer 510 a sequencing of additive layers having permutations within each layer to create the medical modality collimator. The specifications for the medical-modality collimator can be stored in collimator design specification 536, or provide to the control processor across the electronic communication network. Pre-generated permutation sequences 539 may also be stored and accessed by the processor for generating sets of sequences.

In accordance with some embodiments, a computer program application stored in non-volatile memory or computer-readable medium (e.g., register memory, processor cache, RAM, ROM, hard drive, flash memory, CD ROM, magnetic media, etc.) may include code or executable instructions that when executed may instruct and/or cause a controller or processor to perform methods disclosed herein, such as a method to produce a stereolithography file to instruct a 3D printer to manufacture a 3D printed collimator, as described above.

The computer-readable medium may be a non-transitory computer-readable media including all forms and types of memory and all computer-readable media except for a transitory, propagating signal. In one implementation, the non-volatile memory or computer-readable medium may be external memory.

Although specific hardware and methods have been described herein, note that any number of other configurations may be provided in accordance with embodiments of the invention. Thus, while there have been shown, described, and pointed out fundamental novel features of the invention, it will be understood that various omissions, substitutions, and changes in the form and details of the illustrated embodiments, and in their operation, may be made by those skilled in the art without departing from the spirit and scope of the invention. Substitutions of elements from one embodiment to another are also fully intended and contemplated. The invention is defined solely with regard to the claims appended hereto, and equivalents of the recitations therein.

I claim:

1. A method of manufacturing a collimator (134) on a three-dimensional printer (510), the method comprising:
    obtaining design specifications (536) for the collimator, the design specifications including a channel perimeter pattern and an overall collimator thickness;
    determining a first quantity of deposit layer permutation types based on the channel perimeter pattern;
    determining a respective second quantity of permutation layer elements (310, 320, 330) for each respective one of the deposit layer permutations;
    generating respective sets of sequences for each respective one of the deposit layer permutations, the number of sets equal to the respective second quantity for the corresponding deposit layer permutations;
    assembling the respective sets of sequences into a three-dimensional print file (538),
    providing the three-dimensional file to the three-dimensional printer; and
    manufacturing the collimator by depositing additive layers of material based on contents of the three-dimensional file.

2. The method of claim 1, including obtaining the design specifications by one of accessing a data store record and receiving a file.

3. The method of claim 1, including determining the first quantity as a factorial function of the channel perimeter pattern.

4. The method of claim 1, each respective sets of sequences including a series of patterns of individual additive layers to be printed by the three-dimensional printer.

5. The method of claim 1, including:
    pre-generating permutation sequences based on one or more channel perimeter patterns configurations;
    storing the pre-generated permutation sequences in a data record; and
    the generating sets of sequences including accessing the pre-generated permutation sequences (539).

6. The method of claim 1, the generating sets of sequences including:
    defining an initial base permutation sequence based on the first quantity;
    generating a first sequence of permutations, each permutation containing a plurality of non-repeating elements, where the non-repeating element includes multiples of the base permutation sequence;
    subdividing the first sequence into a quantity of consecutive regions equal to the first quantity;
    generating second and more sequences of permutations;
    appending each of the second and more sequences to the first sequence;
    if the first sequence does not include a quantity of permutations that satisfies collimator design requirements based on additive layer thickness of the three-dimensional printer and an overall collimator thickness, then repeat the generation and subdividing steps.

7. A non-transitory computer-readable medium having stored thereon instructions which when executed by a processor cause the processor to perform a method of manufacturing a collimator (134) on a three-dimensional printer (510), the method comprising:
    obtaining design specifications (536) for the collimator, the design specifications including a channel perimeter pattern and an overall collimator thickness;
    determining a first quantity of deposit layer permutation types based on the channel perimeter pattern;
    determining a respective second quantity of permutation layer elements (310, 320, 330) for each respective one of the deposit layer permutations;
    generating respective sets of sequences for each respective one of the deposit layer permutations, the number of sets equal to the respective second quantity for the corresponding deposit layer permutations;
    assembling the respective sets of sequences into a three-dimensional print file (538),
    providing the three-dimensional file to the three-dimensional printer; and
    manufacturing the collimator by depositing additive layers of material based on contents of the three-dimensional file.

8. The medium of claim 7, including instructions to cause the processor to perform the step of obtaining the design specifications by one of accessing a data store record and receiving a file.

9. The medium of claim 7, including instructions to cause the processor to perform the step of determining the first quantity as a factorial function of the channel perimeter pattern.

10. The medium of claim 7, including instructions to cause the processor to perform the step of including in each respective sets of sequences a series of patterns of individual additive layers to be printed by the three-dimensional printer.

11. The medium of claim 7, including instructions to cause the processor to perform the steps of:
pre-generating permutation sequences based on one or more channel perimeter patterns configurations;
storing the pre-generated permutation sequences in a data record; and
the generating sets of sequences including accessing the pre-generated permutation sequences (539).

12. The medium of claim 7, including instructions to cause the processor to perform the step of generating sets of sequences by including:
defining an initial base permutation sequence based on the first quantity;
generating a first sequence of permutations, each permutation containing a plurality of non-repeating elements, where the non-repeating element includes multiples of the base permutation sequence;
subdividing the first sequence into a quantity of consecutive regions equal to the first quantity;
generating second and more sequences of permutations;
appending each of the second and more sequences to the first sequence; and
if the first sequence does not include a quantity of permutations that satisfies collimator design requirements based on additive layer thickness of the three-dimensional printer and an overall collimator thickness, the repeat the generation and subdividing steps.

13. A system for manufacturing a collimator (134) on a three-dimensional printer (510), the system comprising:
the three-dimensional printer in communication with a control processor (520);
the control processor in communication with a data store (530), the data store including executable instructions (532) that cause the control processor to perform a method, the method including:
obtaining design specifications (536) for the collimator, the design specifications including a channel perimeter pattern and an overall collimator thickness;
determining a first quantity of deposit layer permutation types based on the channel perimeter pattern;
determining a respective second quantity of permutation layer elements (310, 320, 330) for each respective one of the deposit layer permutations;
generating respective sets of sequences for each respective one of the deposit layer permutations, the number of sets equal to the respective second quantity for the corresponding deposit layer permutations;
assembling the respective sets of sequences into a three-dimensional print file (538),
providing the three-dimensional file to the three-dimensional printer; and
manufacturing the collimator by depositing additive layers of material based on contents of the three-dimensional file.

14. The system of claim 13, the executable instructions causing the control processor to perform the method by including:
pre-generating permutation sequences based on one or more channel perimeter patterns configurations;
storing the pre-generated permutation sequences in a data record; and
the generating sets of sequences including accessing the pre-generated permutation sequences (539).

15. The system of claim 13, the executable instructions causing the control processor to perform the method by including in the step of generating sets of sequences:
defining an initial base permutation sequence based on the first quantity;
generating a first sequence of permutations, each permutation containing a plurality of non-repeating elements, where the non-repeating element includes multiples of the base permutation sequence;
subdividing the first sequence into a quantity of consecutive regions equal to the first quantity;
generating second and more sequences of permutations;
appending each of the second and more sequences to the first sequence; and
if the first sequence does not include a quantity of permutations that satisfies collimator design requirements based on additive layer thickness of the three-dimensional printer and an overall collimator thickness, then repeat the generation and subdividing steps.

\* \* \* \* \*

UNITED STATES PATENT AND TRADEMARK OFFICE
CERTIFICATE OF CORRECTION

PATENT NO. : 11,327,464 B2  
APPLICATION NO. : 15/733430  
DATED : May 10, 2022  
INVENTOR(S) : Miesher Rodrigues Page 1 of 1

It is certified that error appears in the above-identified patent and that said Letters Patent is hereby corrected as shown below:

In the Specification

In the Detailed Description Section, Column 6, Line 53, "… (e.g., triangular channel …" should read "… (e.g., triangular channel) …"

In the Detailed Description Section, Column 6, Line 62, "Once the sequences for each permutation layer is generated…" should read "Once the sequences for each permutation layer are generated…"

In the Claims

Column 9, Claim 12, Line 40, "… the repeat the generation and subdividing steps." should read "… then repeat the generation and subdividing steps."

Signed and Sealed this  
Twenty-sixth Day of December, 2023

Katherine Kelly Vidal  
*Director of the United States Patent and Trademark Office*